United States Patent
Hoshiyama et al.

(10) Patent No.: US 11,660,042 B2
(45) Date of Patent: May 30, 2023

(54) MAGNETIC RESONANCE IMAGING APPARATUS, METHOD, AND STORAGE MEDIUM

(71) Applicant: CANON MEDICAL SYSTEMS CORPORATION, Otawara (JP)

(72) Inventors: Yutaka Hoshiyama, Nasushiobara (JP); Nami Matsunaga, Utsunomiya (JP); Katsusuke Kyotani, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 44 days.

(21) Appl. No.: 17/308,109

(22) Filed: May 5, 2021

(65) Prior Publication Data

US 2021/0353212 A1    Nov. 18, 2021

(30) Foreign Application Priority Data

May 15, 2020    (JP) .............................. JP2020-085649

(51) Int. Cl.
*A61B 5/00*    (2006.01)
*A61B 5/055*   (2006.01)
*G01R 33/54*   (2006.01)

(52) U.S. Cl.
CPC ............ *A61B 5/4381* (2013.01); *A61B 5/004* (2013.01); *A61B 5/055* (2013.01); *A61B 5/7267* (2013.01); *G01R 33/543* (2013.01)

(58) Field of Classification Search
None
See application file for complete search history.

(56) References Cited

U.S. PATENT DOCUMENTS

| 9,940,713 B1 * | 4/2018 | Bhat ................... G01R 33/3875 |
| 2014/0073907 A1 * | 3/2014 | Kumar ................ A61B 10/0241 |
| | | 600/407 |

(Continued)

FOREIGN PATENT DOCUMENTS

JP    2014-213084 A    11/2014

OTHER PUBLICATIONS

Villers et al., "Magnetic Resonance Assessment of Prostate Localization Variability in Intensity-Modulated Radiotherapy for Prostate Cancer," (Dec. 20040, International Journal of Radiation Oncology*Biology*Physics, vol. 60, Issue 5, Dec. 1, 2004, pp. 1611-1621. (Year: 2004).*

(Continued)

*Primary Examiner* — Yi-Shan Yang
*Assistant Examiner* — Ashish S Jasani
(74) *Attorney, Agent, or Firm* — Oblon, McClelland, Maier & Neustadt, L.L.P.

(57) ABSTRACT

A magnetic resonance imaging apparatus according to an embodiment includes: a coil configured to receive a magnetic resonance signal emitted from a subject due to influence of a radio frequency magnetic field; and processing circuitry. The processing circuitry is configured to detect at least one tissue from among a femoral head, the pelvis, an articular labrum, the pubic symphysis, the urethra, and the apex of the prostate of the subject, from a locator image based on the magnetic resonance signal and corresponding to a range including the prostate of the subject. The processing circuitry is configured to determine a region to be imaged of the prostate of the subject, on the basis of the detected tissue.

12 Claims, 12 Drawing Sheets

(56) References Cited

U.S. PATENT DOCUMENTS

2020/0219262 A1\* 7/2020 Hsiao ................... G06N 3/0445
2020/0258216 A1\* 8/2020 Sharma ................ A61B 5/0037

OTHER PUBLICATIONS

Winkel et al., "A Fully Automated, End-to-End Prostate MRI Workflow Solution Incorporating Dot, Ultrashort Biparametric Imaging and Deep-Learning-based Detection, Classification," (Jan. 2020) MAGNETOM Flash, Issue 76, p. 78-83. (Year: 2020).\*
Horger et al., "The Prostate Dot Engine—a System-Guided and Assisted Workflow to Improve Consistency in Prostate MR Exams," (Jan. 2020) MAGNETOM Flash, Issue 76, p. 73-77. (Year: 2020).\*
Esser et al., "Performance of an Automated Workflow for Magnetic Resonance Imaging of the Prostate Comparison With a Manual Workflow," (Dec. 30, 2019) Invest Radiol, May 2020;55(5):277-284. (Year: 2019).\*

\* cited by examiner

MAGNETIC RESONANCE IMAGING APPARATUS, METHOD, AND STORAGE MEDIUM

CROSS-REFERENCE TO RELATED APPLICATIONS

This application is based upon and claims the benefit of priority from Japanese Patent Application No. 2020-085649, filed on May 15, 2020; the entire contents of which are incorporated herein by reference.

FIELD

Embodiments described herein relate generally to a magnetic resonance imaging apparatus, a method, and a storage medium.

BACKGROUND

Conventionally, with a Magnetic Resonance Imaging (MRI) apparatus, in some situations, before taking a diagnosis-purpose image of a subject, the user manually sets a region to be imaged for the diagnosis-purpose image, within a locator image having been taken during a preliminary scan. Setting the region to be imaged for the main imaging process in this manner will be referred to as a position determining process.

DETAILED DESCRIPTION

Exemplary embodiments of a magnetic resonance imaging apparatus, a method, and a storage medium will be explained in detail below, with reference to the accompanying drawings.

A magnetic resonance imaging apparatus according to an embodiment includes: a coil configured to receive a magnetic resonance signal emitted from a subject due to influence of a radio frequency magnetic field; and processing circuitry. The processing circuitry is configured to detect at least one tissue from among a femoral head, the pelvis, an articular labrum, the pubic symphysis, the urethra, and the apex of the prostate of the subject, from a locator image based on the magnetic resonance signal and corresponding to a range including the prostate of the subject. The processing circuitry is configured to determine a region to be imaged of the prostate of the subject, on the basis of the detected tissue.

Figure 1:
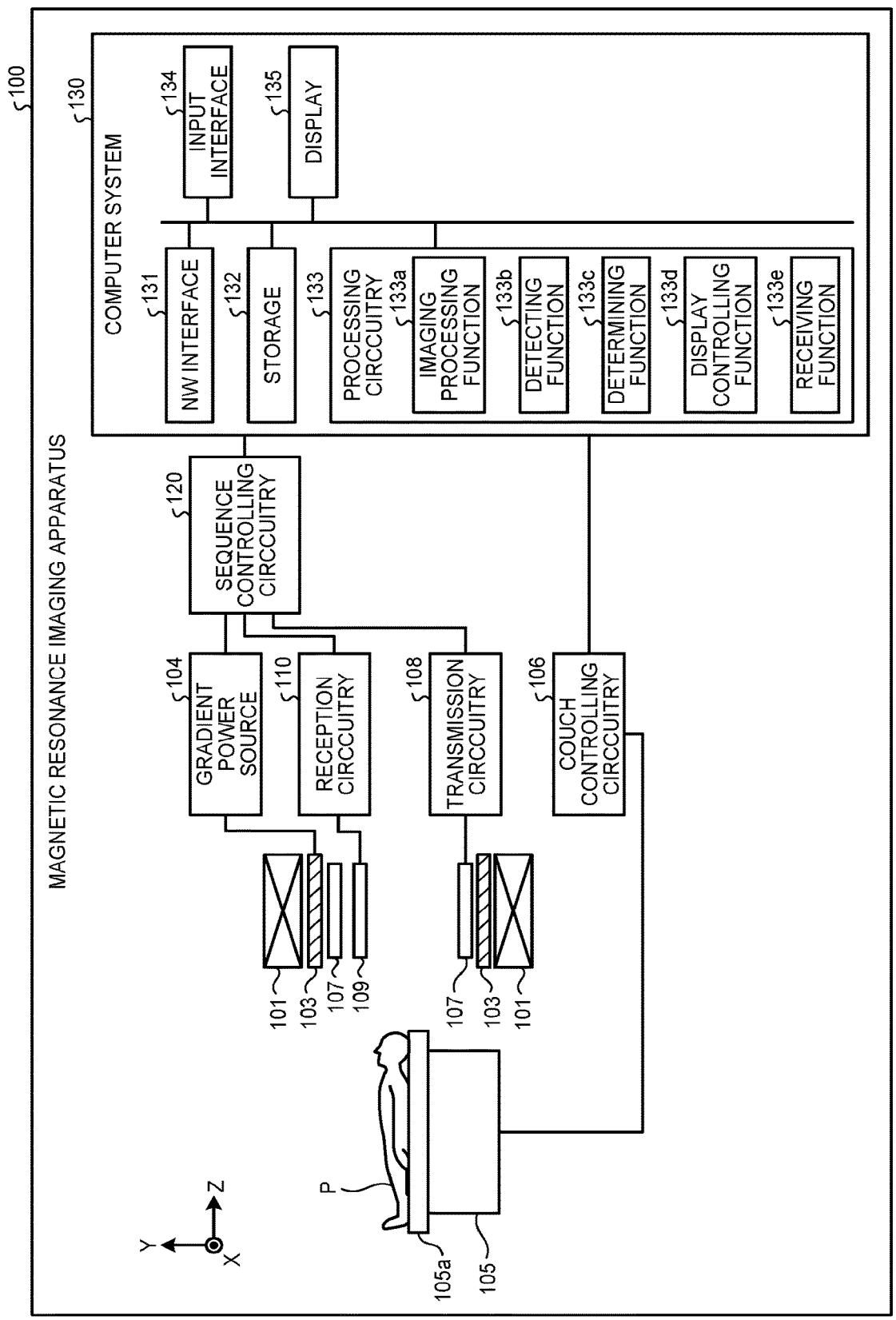
FIG. 1 is a block diagram illustrating an example of a magnetic resonance imaging apparatus according to a first embodiment.

FIG. 1 is a block diagram illustrating an example of a Magnetic Resonance Imaging (MRI) apparatus 100 according to an embodiment. As illustrated in FIG. 1, the magnetic resonance imaging apparatus 100 includes a static magnetic field magnet 101, a static magnetic field power source (not illustrated), a gradient coil 103, a gradient power source 104, a couch 105, couch controlling circuitry 106, a transmission coil 107, transmission circuitry 108, a reception coil 109, reception circuitry 110, sequence controlling circuitry 120, and a computer system 130.

The configuration illustrated in FIG. 1 is merely an example. For instance, any of the functional units in the sequence controlling circuitry 120 and the computer system 130 may be integrated together or separated as appropriate. In the present example, the magnetic resonance imaging apparatus 100 does not include a subject (hereinafter, "patient") P (e.g., a human body).

The X-axis, the Y-axis, and the Z-axis illustrated in FIG. 1 structure an apparatus coordinate system unique to the magnetic resonance imaging apparatus 100. For example, the Z-axis direction coincides with the axial direction of the circular cylinder of the gradient coil 103 and is set along a magnetic flux of a static magnetic field generated by the static magnetic field magnet 101. The Z-axis direction is the same as the longitudinal direction of the couch 105 and is also the same as the head-to-toe direction of the patient P placed on the couch 105. Further, the X-axis direction is set along a horizontal direction orthogonal to the Z-axis direction. The Y-axis direction is set along a vertical direction orthogonal to the Z-axis direction.

The static magnetic field magnet 101 is a magnet formed to have a hollow and substantially circular cylindrical shape and is configured to generate the static magnetic field in the space on the inside thereof. For example, the static magnetic field magnet 101 is a superconductive magnet or the like and is magnetically excited by receiving a supply of an electric current from the static magnetic field power source. The static magnetic field power source is configured to supply the electric current to the static magnetic field magnet 101. In another example, the static magnetic field magnet 101 may be a permanent magnet. In that situation, the magnetic resonance imaging apparatus 100 does not necessarily have to include a magnetic static field power source. Further, the magnetic static field power source may be provided separately from the magnetic resonance imaging apparatus 100.

The gradient coil 103 is a coil formed to have a hollow and substantially cylindrical shape and is arranged on the inside of the static magnetic field magnet 101. The gradient coil 103 is formed by combining together three coils corresponding to the X-, Y-, and Z-axes that are orthogonal to one another. By individually receiving a supply of an electric current from the gradient power source 104, each of the three coils is configured to generate a gradient magnetic field of which the magnetic field intensity changes along the corresponding one of the X-, Y-, and Z-axes. Further, under control of the sequence controlling circuitry 120, the gradient power source 104 is configured to supply the electric currents to the gradient coil 103.

The couch 105 includes a couchtop 105a on which the patient P is placed. Under control of the couch controlling circuitry 106, the couchtop 105a is inserted into an image taking opening, while the patient P (e.g., a person seeking medical attention) is placed thereon. Under control of the computer system 130, the couch controlling circuitry 106 is configured to drive the couch 105 so as to move the couchtop 105a in longitudinal directions and up-and-down directions.

The transmission coil 107 is configured to magnetically excite an arbitrary region of the patient P, by applying a radio frequency magnetic field thereto. The transmission coil 107 is, for example, a whole body coil surrounding the whole body of the patient P. The transmission coil 107 is configured to generate the radio frequency magnetic field by receiving a supply of a Radio Frequency (RF) pulse from the transmission circuitry 108 and to apply the radio frequency magnetic field to the patient P. Under control of the sequence controlling circuitry 120, the transmission circuitry 108 is configured to supply the RF pulse to the transmission coil 107.

The reception coil 109 is arranged on the inside of the gradient coil 103 and is configured to receive magnetic resonance signals (hereinafter, "MR signals") emitted from the patient P due to influence of the radio frequency magnetic field. Upon receipt of the MR signals, the reception coil 109 is configured to output the received MR signals to the reception circuitry 110.

Although FIG. 1 illustrates the configuration in which the reception coil 109 is provided separately from the transmission coil 107, this configuration is merely an example, and possible embodiments are not limited to this configuration. For example, another arrangement is also acceptable in which the reception coil 109 also serves as the transmission coil 107. In the following sections, the transmission coil 107 and the reception coil 109 may collectively be referred to as "coils".

The reception circuitry 110 is configured to generate Magnetic Resonance (MR) data by performing an Analog-to-Digital (A/D) conversion on the analog MR signals output from the reception coil 109. Further, the reception circuitry 110 is configured to transmit the generated MR data to the sequence controlling circuitry 120. Alternatively, the AD conversion may be performed in the reception coil 109. Further, the reception circuitry 110 is also capable of performing arbitrary signal processing besides the AD conversion.

The sequence controlling circuitry 120 is configured to perform an imaging process on the patient P, by driving the gradient power source 104, the transmission circuitry 108, and the reception circuitry 110 on the basis of sequence information transmitted thereto from the computer system 130.

In this situation, the sequence information is information defining a procedure for performing the imaging process. The sequence information defines: the intensity of the electric current to be supplied by the gradient power source 104 to the gradient coil 103 and the timing with which the electric current is to be supplied; the intensity of the RF pulse to be supplied by the transmission circuitry 108 to the transmission coil 107 and the timing with which the RF pulse is to be applied; the timing with which the MR signal is to be detected by the reception circuitry 110; and the like. The sequence information varies depending on the range of the region subject to the imaging process selected from the body of the patient P.

The sequence controlling circuitry 120 may be realized by using a processing circuit or may be realized by a combination of software and hardware.

Further, upon receipt of the MR data from the reception circuitry 110 as a result of imaging the patient P by driving the gradient power source 104, the transmission circuitry 108, and the reception circuitry 110, the sequence controlling circuitry 120 is configured to transfer the received MR data to the computer system 130.

The computer system 130 is configured to control the entirety of the magnetic resonance imaging apparatus 100 and to generate MR images, among other processes. As illustrated in FIG. 1, the computer system 130 includes a network (NW) interface 131, storage 132, processing circuitry 133, an input interface 134, and a display 135.

The NW interface 131 is configured to communicate with the sequence controlling circuitry 120 and the couch controlling circuitry 106. For example, the NW interface 131 is configured to transmit the sequence information to the sequence controlling circuitry 120. Further, the NW interface 131 is configured to receive the MR data from the sequence controlling circuitry 120.

The storage 132 is configured to store therein the MR data received by the NW interface 131, k-space data arranged in a k-space by the processing circuitry 133 (explained later), image data generated by the processing circuitry 133, and the like. For example, the storage 132 is a semiconductor memory element such as a Random Access Memory (RAM) or a flash memory, or a hard disk, an optical disk, or the like.

The input interface 134 is configured to receive inputs of various types of instructions and information from an operator. For example, the input interface 134 is realized by using a trackball, a switch button, a mouse, a keyboard, a touchpad on which an input operation can be performed by touching an operation surface thereof, a touch screen in which a display screen and a touchpad are integrally formed, contactless input circuitry using an optical sensor, audio input circuitry, and/or the like. The input interface is connected to the processing circuitry 133 and is configured to convert the input operations received from the operator into electrical signals and to output the electrical signals to the processing circuitry 133. In the present disclosure, the input interface does not necessarily have to include one or more physical operational component parts such as a mouse, a keyboard, and/or the like. Examples of the input interface include, for instance, an electrical signal processing circuitry configured to receive electrical signals corresponding to input operations from an external input device provided separately from the computer system 130 and to output the electrical signals to control circuitry.

Under control of the processing circuitry 133, the display 135 is configured to display a Graphical User Interface (GUI) used for receiving an input of image taking conditions, magnetic resonance images generated by the processing circuitry 133, and the like. For example, the display 135 is a display such as a liquid crystal display monitor.

The processing circuitry 133 is configured to control the entirety of the magnetic resonance imaging apparatus 100. More specifically, the processing circuitry 133 includes, in an example, an imaging processing function 133a, a detecting function 133b, a determining function 133c, a display controlling function 133d, and a receiving function 133e. The imaging processing function 133a is an example of an imaging processing unit. The detecting function 133b is an example of a detecting unit. The determining function 133c is a part of a determining unit. The display controlling function 133d is an example of a display controlling unit. The receiving function 133e is an example of a receiving unit.

In this situation, for example, processing functions of the constituent elements of the processing circuitry 133, namely, the imaging processing function 133a, the detecting function 133b, the determining function 133c, the display controlling function 133d, and the receiving function 133e, are stored in the storage 132 in the form of computer-executable programs. For example, the processing circuitry 133 is configured to realize the functions corresponding to the programs, by reading and executing the programs from the storage 132. In other words, the processing circuitry 133 that has read the programs has the functions illustrated within the processing circuitry 133 in FIG. 1. Although the example was explained with reference to FIG. 1 in which the single piece of processing circuitry is configured to realize the processing functions implemented by the imaging processing function 133a, the detecting function 133b, the determining function 133c, the display controlling function 133d, and the receiving function 133e, another arrangement is also acceptable in which the processing circuitry 133 is structured by combining together a plurality of pieces of independent processing circuitry, so that the functions are realized as a result of the pieces of processing circuitry executing the programs. Further, although the example was explained with reference to FIG. 1 in which the single storage (the storage 132) has stored therein the programs corresponding to the processing functions, another arrangement is also acceptable in which a plurality of storage are provided in a distributed manner, so that the processing circuitry 133 reads a corresponding program from each of the individual storage.

The imaging processing function 133a is configured to perform imaging processes to take magnetic resonance images, by controlling functional units of the magnetic resonance imaging apparatus 100. For example, the imaging processing function 133a is configured to generate the sequence information, to acquire the MR data, to generate the k-space data, and to generate the magnetic resonance images.

More specifically, the imaging processing function 133a is configured to generate the sequence information defining the procedure of an imaging process in accordance with the type of a magnetic resonance image to be taken and a region to be imaged and to further transmit the generated sequence information to the sequence controlling circuitry 120 via the NW interface 131. The sequence controlling circuitry 120 is configured to execute any of various types of pulse sequences on the basis of the sequence information generated by the imaging processing function 133a.

Further, the imaging processing function 133a is configured to acquire, from the sequence controlling circuitry 120 via the NW interface 131, the MR data converted from the MR signal emitted from the patient P as a result of executing any of the various types of pulse sequences. Further, the imaging processing function 133a is configured to arrange the acquired MR data according to a phase encode amount and/or a frequency encode amount applied by the gradient magnetic field. The MR data arranged in the k-space will be referred to as k-space data. The k-space data is saved in the storage 132.

Further, the imaging processing function 133a is configured to generate the magnetic resonance image on the basis of the k-space data stored in the storage 132. For example, the imaging processing function 133a is configured to generate the magnetic resonance image by performing a reconstructing process such as Fourier transform on the k-space data. The imaging processing function 133a is configured to save the generated magnetic resonance image in the storage 132, for example.

In the present embodiment, the imaging processing function 133a is configured to perform an imaging process to take a position-determining-purpose magnetic resonance image before a main imaging process. The position-determining-purpose magnetic resonance image may be referred to as a locator image or a scout image and is an image used for determining the position of an imaged cross-sectional plane for the main imaging process. The main imaging process is an imaging process to take one or more diagnosis-purpose magnetic resonance images.

In the present embodiment, it is assumed that the position-determining-purpose magnetic resonance image is a magnetic resonance image obtained by imaging a range including the prostate of the patient P. In other words, the position-determining-purpose magnetic resonance image corresponds to the range including the prostate of the patient P and is based on the magnetic resonance signal received by the reception coil 109. Further, the position-determining-purpose magnetic resonance image may be a three-dimensional image or may be two-dimensional multi-slice images. Further, the position-determining-purpose magnetic resonance image may be a rougher image having fewer pixels than the diagnosis-purpose magnetic resonance images.

Alternatively, the position-determining-purpose magnetic resonance image may be a high-definition three-dimensional magnetic resonance image. In that situation, the diagnosis-purpose three-dimensional magnetic resonance images may also serve as the position-determining-purpose magnetic resonance image.

Further, in the present embodiment, the diagnosis-purpose magnetic resonance images taken in the main imaging process are two-dimensional magnetic resonance images to be used in a diagnosing process on the prostate of the patient P. More specifically, in the present embodiment, in the main imaging process, three types of diagnosis-purpose two-dimensional magnetic resonance images are taken in the main imaging process, namely, an axial image (a body-axis cross-sectioning image), a sagittal image (a sagittal cross-section image), and a coronal image (a coronal cross-section image). However, the diagnosis-purpose magnetic resonance images do not necessarily have to include all of the axial image, the sagittal image, and the coronal image. It is sufficient when at least one of the three types of images is included.

The regions to be imaged for taking the diagnosis-purpose two-dimensional magnetic resonance images is determined by the determining function 133c (explained later). The imaging processing function 133a is configured to generate the sequence information on the basis of the region to be imaged determined by the determining function 133c and to perform the main imaging process. Further, when the user changes the position, the size, the tilt, or the like of a region to be imaged 70 determined by the determining function 133c, the imaging processing function 133a is configured to generate sequence information on the basis of the post-change region to be imaged 70 and to perform the main imaging process.

The detecting function 133b is configured to detect at least one tissue from among the femoral heads, the pelvis, articular labra, the pubic symphysis, the urethra, and the apex of the prostate of the patient P, from the position-determining-purpose magnetic resonance image taken of a range including the prostate of the patient P.

In the present embodiment, it is assumed that the detecting function 133b is configured to detect the femoral heads, the pelvis, the articular labra, and the pubic symphysis of the patient P. The femoral heads, the pelvis, the articular labra, and the pubic symphysis are bones positioned in the surroundings of the prostate. In the present embodiment, both bones and cartilage will simply be referred to as bones.

What can be detected is not limited to the above examples. The detecting function 133b may be configured detect, for example, all or only one of the femoral heads, the pelvis, the articular labra, the pubic symphysis, the urethra, and the apex of the prostate of the patient P. Further, when two or more sites selected from among the femoral heads, the pelvis, the articular labra, the pubic symphysis, the urethra, and the apex of the prostate of the patient P are to be detected, it is not necessary to detect all of these sites. In other words, for example, the detecting function 133b is configured to detect at least one of the femoral heads, the pelvis, the articular labra, the pubic symphysis, the urethra, and the apex of the prostate of the patient P.

As for the method for detecting the tissues such as the femoral heads from the position-determining-purpose magnetic resonance image, for example, it is possible adopt an image processing method such as template matching. In that situation, it is assumed, for example, that the storage 132 has stored therein template images of the femoral heads, the pelvis, the articular labrum, the pubic symphysis, the urethra, and the apex of the prostate. On the basis of the template images read from the storage 132, the detecting function 133b is configured to detect image regions rendering the tissues subject to the detection, from a position-determining-purpose magnetic resonance image 80.

Further, possible methods for detecting the tissues such as the femoral heads from the position-determining-purpose magnetic resonance image are not limited to template matching. For example, as for the method for detecting the tissues such as the femoral heads from the position-determining-purpose magnetic resonance image, the detecting function 133b may adopt a method based on deep learning or other types of machine learning. In that situation, the detecting function 133b is configured to detect at least one tissue from among the femoral heads, the pelvis, the articular labra, the pubic symphysis, the urethra, and the apex of the prostate of the patient P from the position-determining-purpose magnetic resonance image, by inputting the position-determining-purpose magnetic resonance image to a trained model stored in the storage 132.

It is assumed that the trained model is a model trained while keeping magnetic resonance images in correspondence with image regions each rendering at least one of a femoral head, the pelvis, an articular labrum, the pubic symphysis, the urethra, and the apex of the prostate within the magnetic resonance images. The trained model is generated by using a method based on deep learning or other types of machine learning. The magnetic resonance images used by the trained model for the training purpose will be referred to as training-purpose magnetic resonance images.

Figure 2:
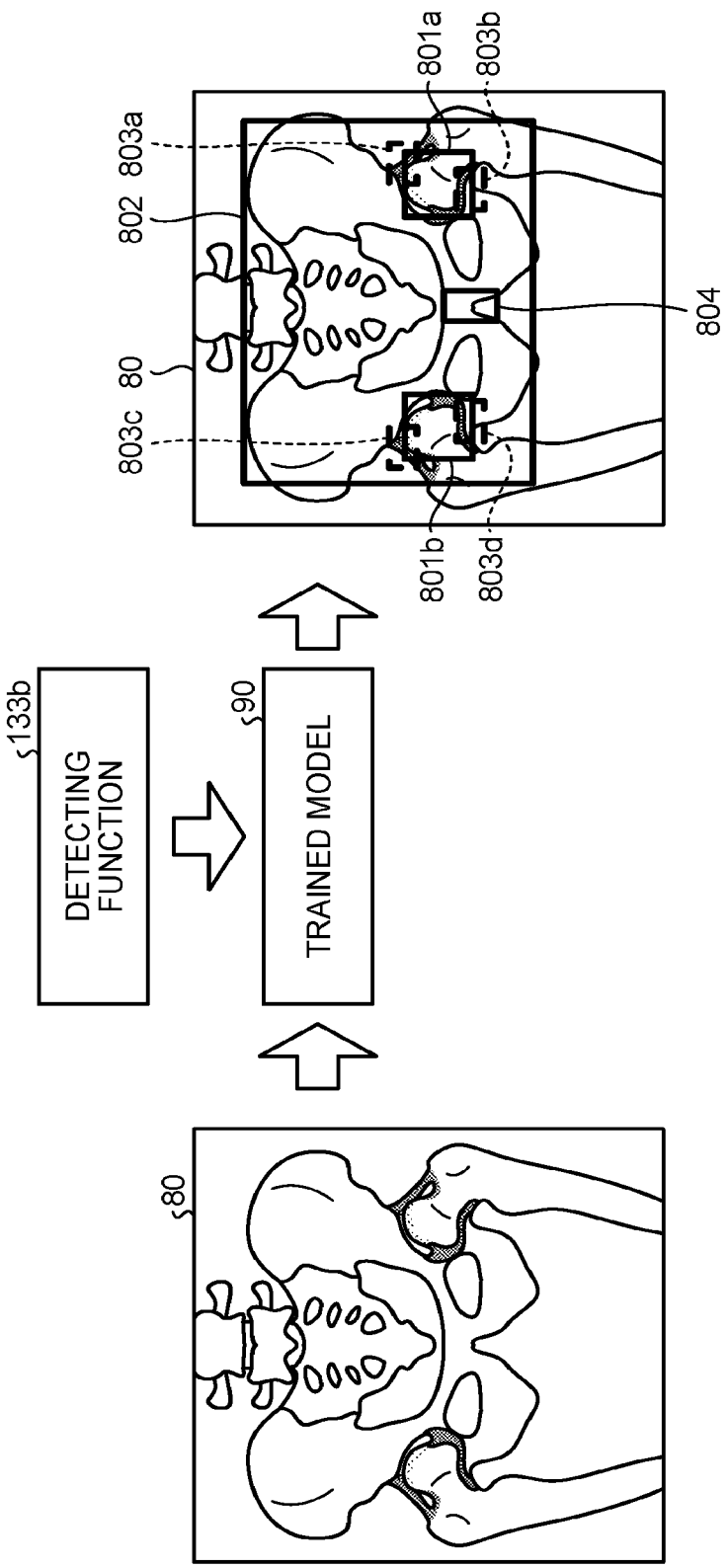
FIG. 2 is a drawing for explaining an example of a trained model according to the first embodiment.

FIG. 2 is a drawing for explaining an example of a trained model 90 according to the present embodiment. As illustrated in FIG. 2, the detecting function 133b inputs the position-determining-purpose magnetic resonance image 80 to the trained model 90. After that, the trained model 90 outputs, as a detection result, an image region within the position-determining-purpose magnetic resonance image 80 that renders the femoral heads, the pelvis, the articular labra, and the pubic symphysis.

In the example in FIG. 2, the trained model 90 is configured to output coordinates in the position-determining-purpose magnetic resonance image 80 regarding image regions 801a and 801b rendering the femoral heads, an image region 802 rendering the pelvis, image regions 803a to 803d rendering the articular labra, and an image region 804 rendering the pubic symphysis. Although FIG. 2 indicates the image regions 801a, 801b, 802, 803a to 803d, and 804 with rectangles for the sake of convenience in the explanation, the trained model 90 may, for example, output the coordinates of the individual pixels contained in the image regions 801a, 801b, 802, 803a to 803d, and 804 within the position-determining-purpose magnetic resonance image 80.

Although FIG. 2 displays the position-determining-purpose magnetic resonance image 80 as a coronal image, the trained model 90 is configured to detect the image regions 801a from cross-sectional planes taken in other directions of the position-determining-purpose magnetic resonance image 80. Further, the trained model 90 may further output an image region rendering the urethra and the apex of the prostate within the position-determining-purpose magnetic resonance image 80.

Further, the detecting function 133b is configured to detect the prostate of the patient P from the position-determining-purpose magnetic resonance image 80 taken of a range including the prostate of the patient P. For the detection of the prostate also, the detecting function 133b may adopt an image processing method such as template matching. For example, it is assumed that the storage 132 has stored therein a template image of the prostate. On the basis of the template image read from the storage 132, the detecting function 133b is configured to detect an image region rendering the prostate within the position-determining-purpose magnetic resonance image 80.

Alternatively, the detecting function 133b may be configured to detect the prostate by using a trained model. The trained model 90 used for detecting the femoral heads and the like may further have the function of detecting the prostate. It is also acceptable to use another trained model designed for detecting the prostate.

The detecting function 133b is configured to send the results of detecting the tissues such as the femoral heads in the surroundings of the prostate and the prostate to the determining function 133c.

Returning to the description of FIG. 1, the determining function 133c is configured to determine regions to be imaged to be used for taking the diagnosis-purpose magnetic resonance images, on the basis of at least one tissue from among the femoral heads, the pelvis, the articular labra, the pubic symphysis, the urethra, and the apex of the prostate of the patient P detected by the detecting function 133b. In the present embodiment, the determining function 133c is configured to determine the regions to be used for taking the diagnosis-purpose magnetic resonance images, on the basis of the femoral heads, the pelvis, the articular labra, and the pubic symphysis of the patient P detected by the detecting function 133b. As mentioned above, in the present embodiment, the diagnosis-purpose magnetic resonance images are the three-types of two-dimensional magnetic resonance images, namely, an axial image, a sagittal image, and a coronal image.

The regions to be imaged in the axial image, the sagittal image, and the coronal image are specified by a slice direction, a slice center, a slice width, and a rotation amount of an imaged cross-sectional plane in the in-plane direction. The determining function 133c is configured to determine at least one of: the slice direction, the slice center, the slice width, and the rotation amount of the imaged cross-sectional plane in the in-plane direction, to be used for taking the diagnosis-purpose magnetic resonance images. It is assumed that the determining function 133c of the present embodiment is configured to determine all of the slice direction, the slice center, the slice width, and the rotation amount of the imaged cross-sectional plane in the in-plane direction. Alternatively, the determining function 133c may determine only one or more of these factors.

Figure 3:
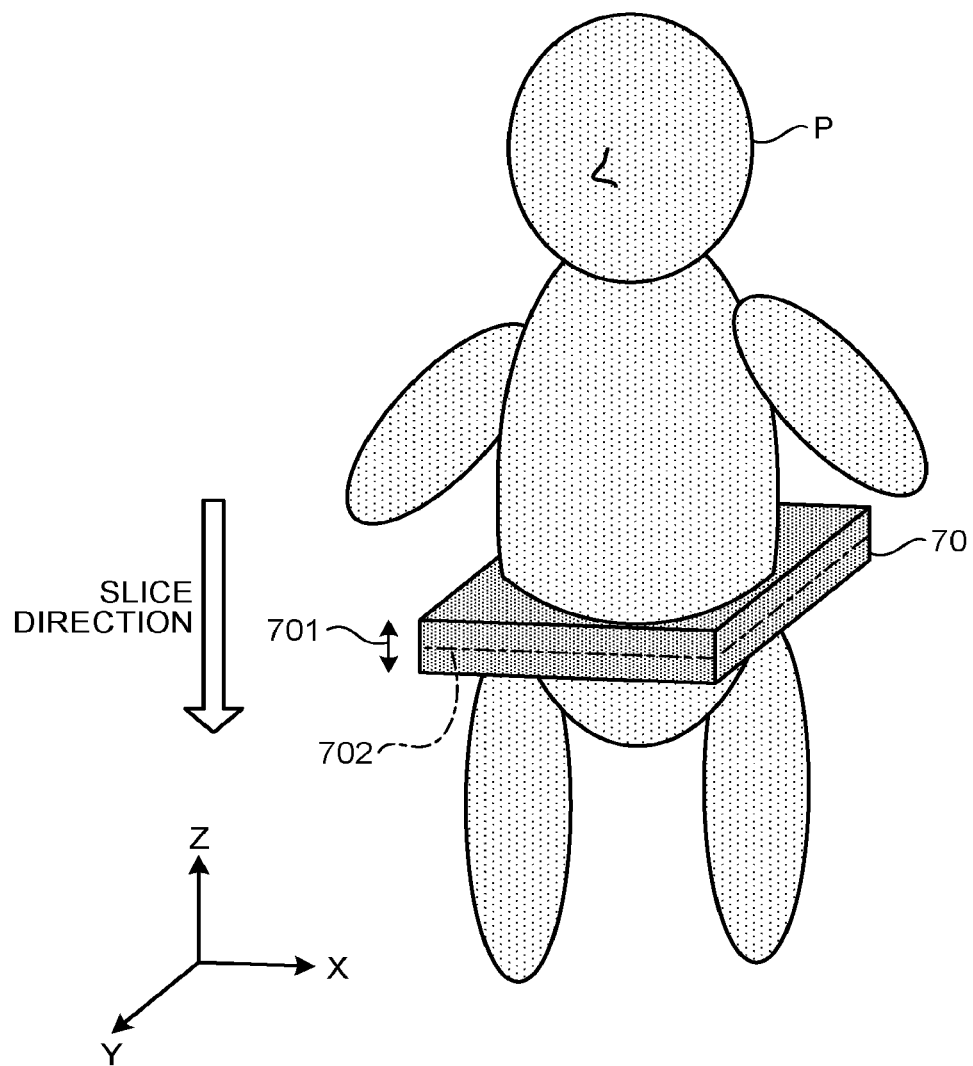
FIG. 3 is a drawing for explaining an example of a region to be imaged for taking a two-dimensional axial image according the first embodiment.

FIG. 3 is a drawing for explaining an example of the region to be imaged 70 for taking a two-dimensional axial image according to the present embodiment. The directions of the X-, Y-, and Z-axes in FIG. 3 indicate the directions of the X-, Y-, and Z-axes in the situation where the patient P is placed on the couch 105 illustrated in FIG. 1.

The region to be imaged 70 may also be referred to as a slice. As illustrated in FIG. 3, the direction perpendicular to the plane of the region to be imaged 70 is referred to as a slice direction. In the axial image, the slice direction is the direction extending along the head-to-toe direction of the patient P.

Further, a slice width 701 is the thickness of the region to be imaged 70. The slice width 701 may be referred to as a slice coverage. Further, a slice center 702 is the center of the region to be imaged 70 in terms of the width direction.

Figure 4:
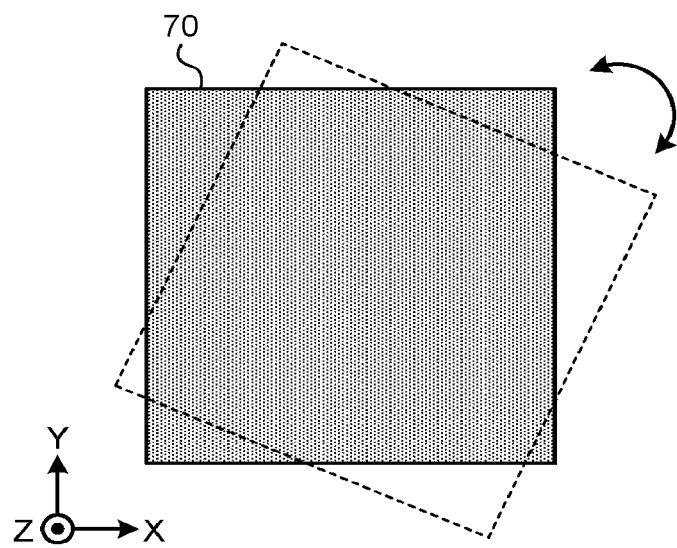
FIG. 4 is a drawing for explaining an example of rotating an imaged cross-sectional plane in an in-plane direction according to the first embodiment.

Further, FIG. 4 is a drawing for explaining an example of rotating the imaged cross-sectional plane in the in-plane direction according to the present embodiment. The in-plane direction of the imaged cross-sectional plane is the direction of the plane parallel to the plane of the region to be imaged 70. The rotation amount of the imaged cross-sectional plane in the in-plane direction is the rotation amount of the region to be imaged 70 on the XY plane defined by the X-axis and the Y-axis in FIG. 3. The rotation amount of the region to be imaged 70 on the XY plane may be expressed, for example, with an angle formed by the Y-axis direction of the magnetic resonance imaging apparatus 100 and the lengthwise sides of the region to be imaged 70 or with an angle formed by the X-axis direction of the magnetic resonance imaging apparatus 100 and the widthwise sides of the region to be imaged 70.

Although FIGS. 3 and 4 illustrate the example with the axial image, also at the times of taking a sagittal image and a coronal image, regions to be imaged 70 are each defined by a slice direction, a slice center, a slice width, and a rotation amount of an imaged cross-sectional plane in the in-plane direction.

Figure 5:
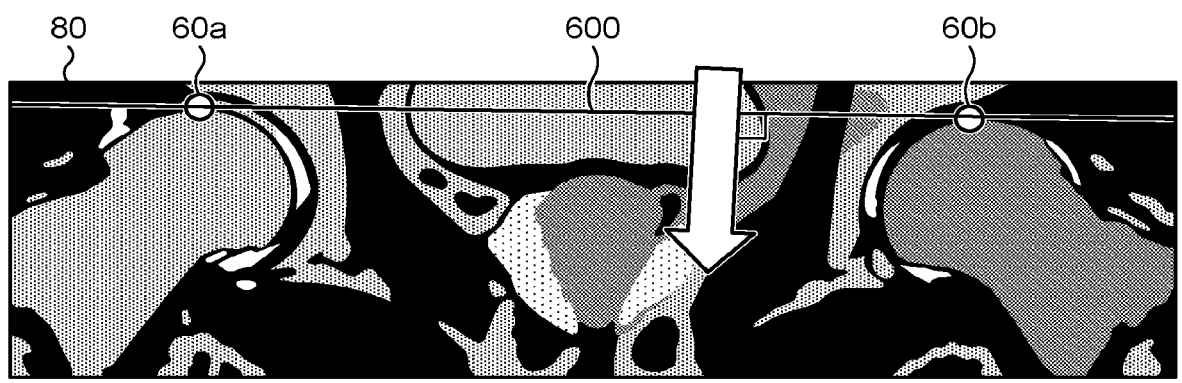
FIG. 5 is a drawing illustrating an example of a method for determining a slice direction of an axial image according to the first embodiment.

FIG. 5 is a drawing illustrating an example of a method for determining the slice direction of an axial image according to the present embodiment. FIG. 5 illustrates an example with a coronal cross-section of a position-determining-purpose magnetic resonance image 80. As illustrated in FIG. 5, the determining function 133c is configured to determine the direction perpendicular to a line segment 600 passing through respective upper end parts 60a and 60b of the two femoral heads in the position-determining-purpose magnetic resonance image 80 detected by the detecting function 133b, as the slice direction for taking the axial image.

Further, on the basis of the positions of the two femoral heads and the position of the pubic symphysis detected by the detecting function 133b, the determining function 133c is configured to determine the slice width 701 and the slice center 702 of the axial image.

Figure 6:
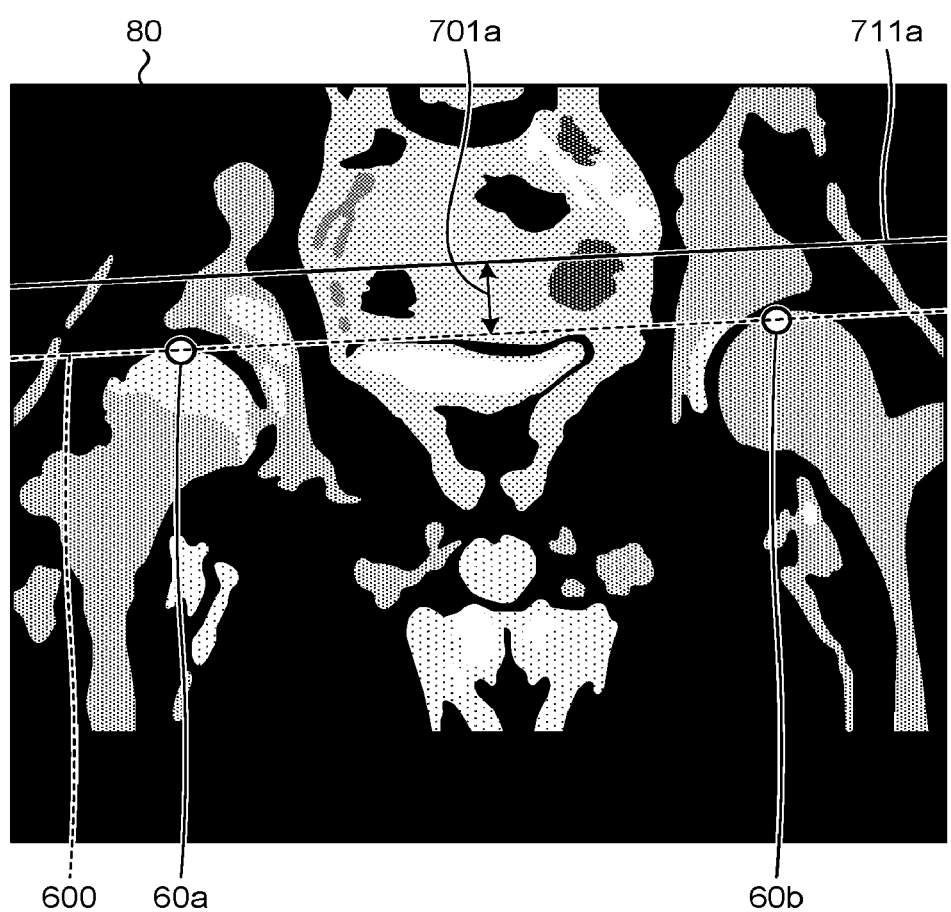
FIG. 6 is a drawing illustrating an example of a method for determining a slice upper end of an axial image according to the first embodiment.
Figure 7:
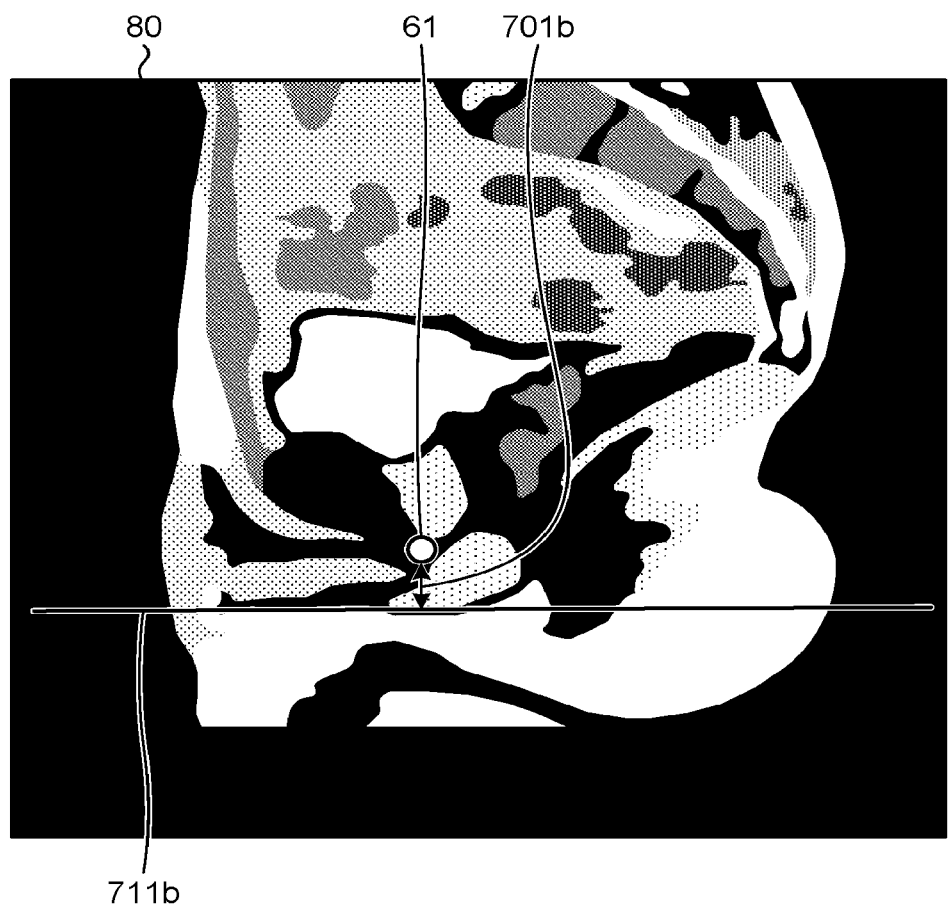
FIG. 7 is a drawing illustrating an example of a method for determining a slice lower end of an axial image according to the first embodiment.

FIG. 6 is a drawing illustrating an example of a method for determining a slice upper end 711a of an axial image according to the present embodiment. FIG. 7 is a drawing illustrating an example of a method for determining a slice lower end 711b of an axial image according to the present embodiment. The interval between the slice upper end 711a and the slice lower end 711b is the slice width 701. FIG. 6 illustrates the example with a coronal cross-section of a position-determining-purpose magnetic resonance image 80. FIG. 7 illustrates the example with a sagittal cross-section of a position-determining-purpose magnetic resonance image 80.

By using the positions of the two femoral heads as a reference, the determining function 133c is configured to determine the slice upper end 711a. In one example, as illustrated in FIG. 6, the determining function 133c determines a line segment obtained by translating the line segment 600 passing through the respective upper end parts 60a and 60b of the two femoral heads by a first distance 701a in the direction toward the head of the patient P, as the slice upper end 711a. The first distance 701a may be 20 mm, for example, but possible embodiments are not limited to this example.

Further, by using the position of the pubic symphysis as a reference, the determining function 133c is configured to determine the slice lower end 711b. In one example, as illustrated in FIG. 7, the determining function 133c determines a line segment positioned apart from a lower end 61 of the pubic symphysis by a second distance 701b in the direction toward the legs of the patient P, as the slice lower end 711b. The second distance 701b may be 10 mm, for example, but possible embodiments are not limited to this example. Although the line segment 600 and the slice upper end 711a are omitted from FIG. 7, it is assumed that the slice lower end 711b is parallel to the line segment 600 and to the slice upper end 711a.

Further, the position in the middle between the slice upper end 711a and the slice lower end 711b serves as the slice center 702 for taking the axial image.

Further, although FIG. 7 illustrates the example in which the pubic symphysis is used as the reference for determining the slice lower end 711b for taking the axial image, the pubic symphysis may also be used for other purposes. For example, the determining function 133c may determine a slice width 701 for taking a coronal image, on the basis of the position of the pubic symphysis in the front-and-back direction of the body of the patient P.

Further, on the basis of four articular labra detected by the detecting function 133b, the determining function 133c is configured to determine the rotation amount of the imaged cross-sectional plane in the in-plane direction. In some situations, the X-axis, Y-axis, and Z-axis directions of the magnetic resonance imaging apparatus 100 may be different from one or more of the width direction, the front-and-back direction, and the body-axis direction of the patient P rendered in the position-determining-purpose magnetic resonance image 80. For example, the determining function 133c may determine the direction perpendicular to a line segment connecting together two articular labra positioned so as to face each other along the width direction of the body of the patient P, as the body-axis direction of the patient P and may determine the rotation amount of the imaged cross-sectional plane in the in-plane direction so that the body-axis direction matches the Z-axis direction of the position-determining-purpose magnetic resonance image 80.

Figure 8:
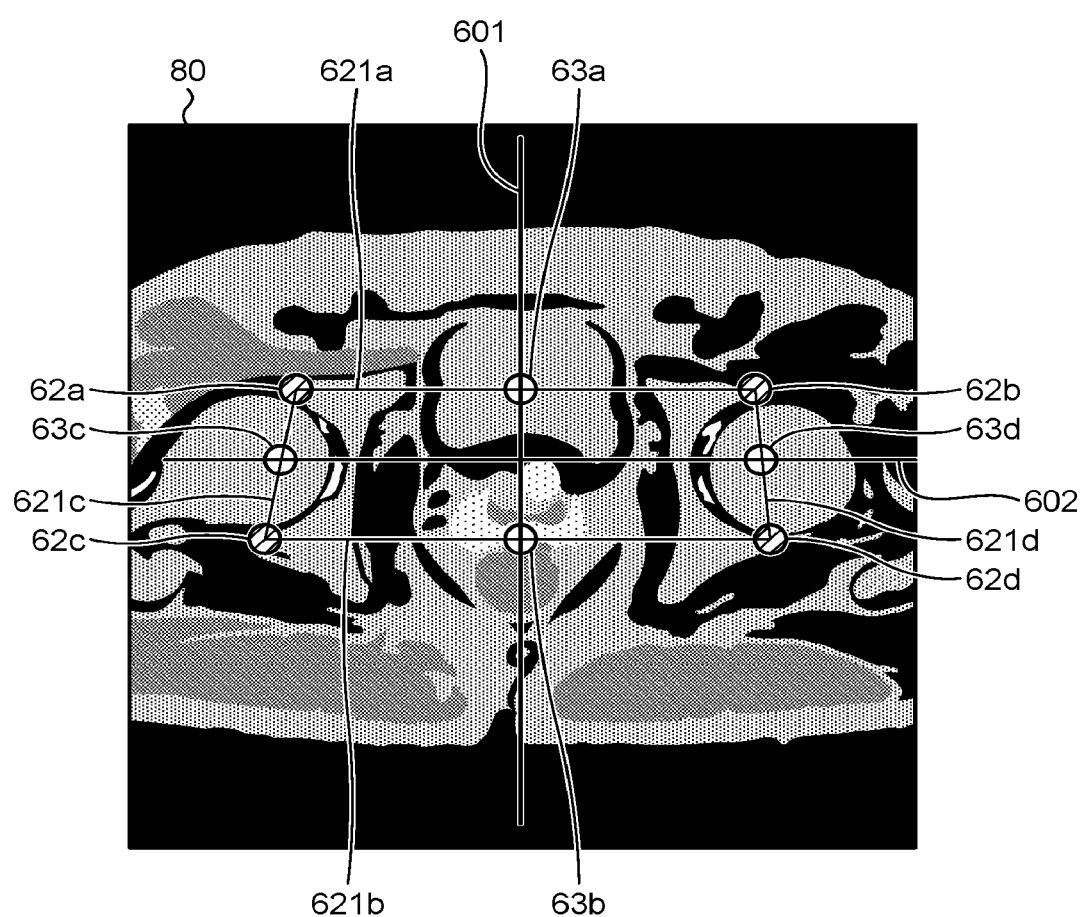
FIG. 8 is a drawing illustrating an example of a method for determining a rotation amount of an axial image in an in-plane direction according to the first embodiment.

Possible methods for determining the rotation amount of the imaged cross-sectional plane in the in-plane direction are not limited to the method described above. FIG. 8 is a drawing illustrating another example of a method for determining a rotation amount of an axial image in the in-plane direction according to the present embodiment. FIG. 8 illustrates the example with a body-axis cross-sectioning plane of a position-determining-purpose magnetic resonance image 80. In FIG. 8, articular labra 62a and 62b are the articular labra on the front side of the patient P. Further, articular labra 62c and 62d are the articular labra on the back side of the patient P. The articular labra 62a to 62d are detected by the detecting function 133b.

For example, the determining function 133c is configured to obtain a middle point 63a of a line segment 621a connecting together the articular labrum 62a and the articular labrum 62b facing each other along the width direction of the body of the patient P. Further, the determining function 133c is configured to obtain a middle point 63b of a line segment 621b connecting together the articular labrum 62c and the articular labrum 62d facing each other along the width direction of the body of the patient P. In addition, the determining function 133c is configured to obtain a middle point 63c of a line segment 621c connecting together the articular labrum 62a and the articular labrum 62c facing each other along the front-and-back direction of the body of the patient P. Also, the determining function 133c is configured to obtain a middle point 63d of a line segment 621d connecting together the articular labrum 62b and the articular labrum 62d facing each other along the front-and-back direction of the body of the patient P.

After that, for example, the determining function 133c is configured to obtain a line segment 601 passing through the middle point 63a and the middle point 63b. Further, the determining function 133c is configured to obtain a line segment 602 passing through the middle point 63c and the middle point 63d. For example, the determining function 133c is configured to calculate the rotation amount of the axial image in the in-plane direction so that the lengthwise direction of the region to be imaged 70 is parallel to the line segment 601. Alternatively, the determining function 133c may be configured to calculate a rotation amount of the axial image in the in-plane direction so that the widthwise direction of the region to be imaged 70 is parallel to the line segment 602.

Further, the determining function 133c is configured to determine slice directions of diagnosis-purpose sagittal and coronal images, on the basis of the positions of the articular labra 62a to 62d in the position-determining-purpose magnetic resonance image 80 detected by the detecting function 133b.

Figure 9:
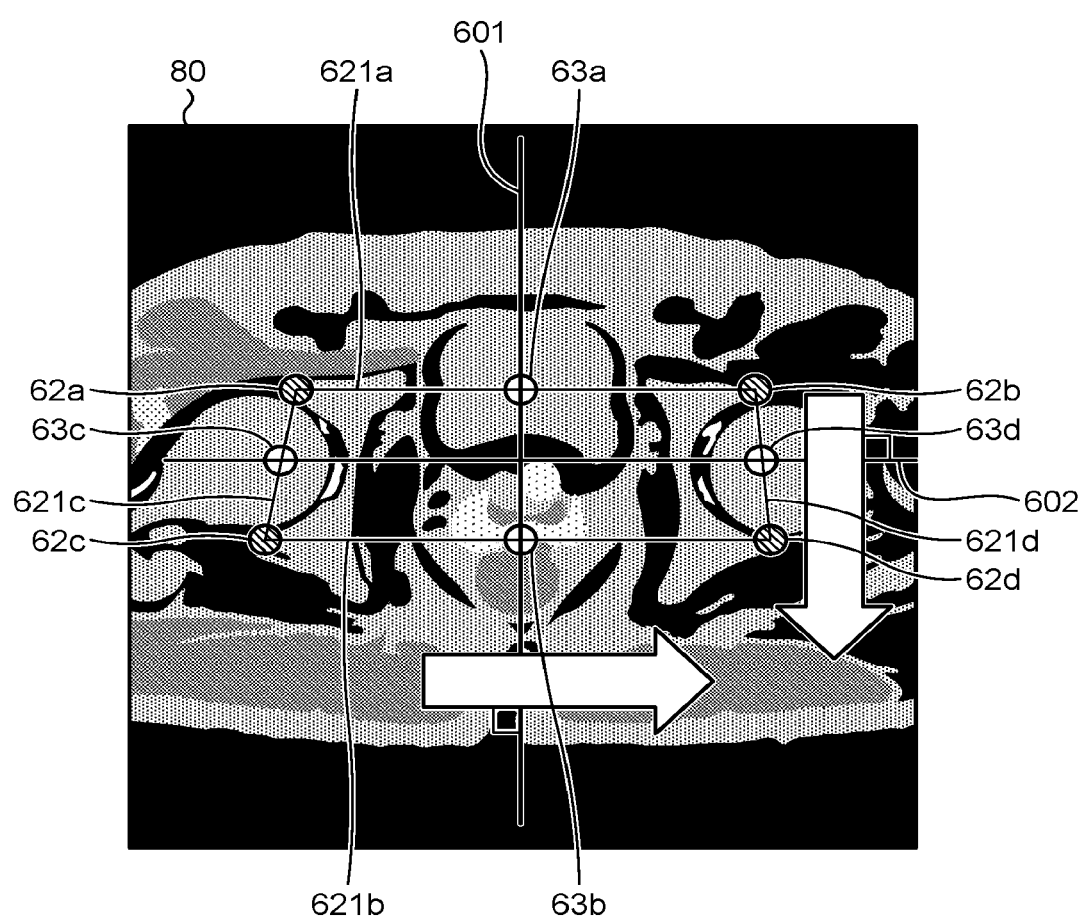
FIG. 9 is a drawing illustrating an example of a method for determining slice directions of a sagittal image and a coronal image according to the first embodiment.

FIG. 9 is a drawing illustrating an example of a method for determining the slice directions of the sagittal image and the coronal image according to the present embodiment. FIG. 9 illustrates the example with a body-axis cross-sectioning plane of the position-determining-purpose magnetic resonance image 80.

The determining function 133c is configured to obtain the middle point 63a of the line segment 621a connecting together the articular labrum 62a and the articular labrum 62b facing each other along the width direction of the body of the patient P. Further, the determining function 133c is configured to obtain the middle point 63b of the line segment 621b connecting together the articular labrum 62c and the articular labrum 62d facing each other along the width direction of the body of the patient P. In addition, the determining function 133c is configured to obtain the middle point 63c of the line segment 621c connecting together the articular labrum 62a and the articular labrum 62c facing each other along the front-and-back direction of the body of the patient P. Also, the determining function 133c is configured to obtain the middle point 63d of the line segment 621d connecting together the articular labrum 62b and the articular labrum 62d facing each other along the front-and-back direction of the body of the patient P.

After that, the determining function 133c is configured to obtain the line segment 601 passing through the middle point 63a and the middle point 63b. In addition, the determining function 133c is configured to obtain the line segment 602 passing through the middle point 63c and the middle point 63d.

The determining function 133c is configured to determine the direction perpendicular to the line segment 601 as the slice direction for taking the diagnosis-purpose sagittal image. Also, the determining function 133c is configured to determine the direction perpendicular to the line segment 602 as the slice direction for taking the diagnosis-purpose coronal image.

Further, the determining function 133c is configured to determine the slice center 702 to be in the position passing through the center of the prostate detected by the detecting function 133b. Further, when the slice center 702 determined on the basis of the detected position of the prostate is apart from the position of the pubic symphysis of the patient P detected by the detecting function 133b by a distance equal to or longer than a prescribed length, the determining function 133c is configured to correct the position of the slice center 702 on the basis of the detected position of the pubic symphysis. The prescribed length is not particularly limited, and may be set by a technologist or the like or may be determined in advance.

Generally speaking, when the detected position of the prostate is accurate, the center of the prostate in terms of the width direction of the patient P substantially matches the center of the pubic symphysis in terms of the width direction of the patient P. When, however, the detecting function 133b erroneously detects the position of the prostate, or the like, the slice center 702 determined on the basis of the detected position of the prostate may be apart, in some situations, from the position of the pubic symphysis of the patient P detected by the detecting function 133b by a distance equal to or longer than the prescribed length.

Figure 10:
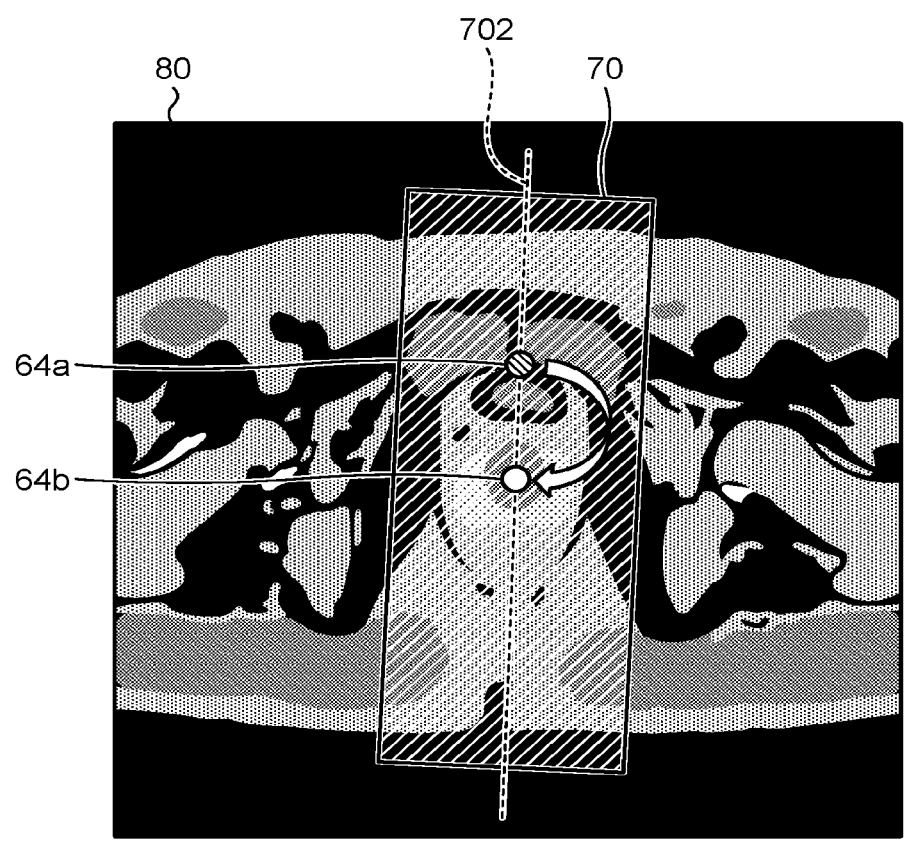
FIG. 10 is a drawing illustrating an example of a method for determining a slice center for taking a sagittal image according to the first embodiment.

FIG. 10 is a drawing illustrating an example of a method for determining the slice center for taking a sagittal image according to the present embodiment. FIG. 10 illustrates the example with a body-axis cross-sectioning plane of the position-determining-purpose magnetic resonance image 80. The determining function 133c corrects the position of the slice center 702 so that the slice center 702 is positioned so as to pass through an end part 64a on the front-side of the patient P and an end part 64b on the back-side of the patient P, of the pubic symphysis rendered in the position-determining-purpose magnetic resonance image 80.

The process of correcting the slice center 702 is not requisite, and the determining function 133c may adopt the slice center 702 determined by using the center of the prostate as a reference.

Further, the determining function 133c is configured to determine the slice width 701 for taking the sagittal image, on the basis of characteristic points of the pelvis of the patient P detected by the detecting function 133b.

Figure 11:
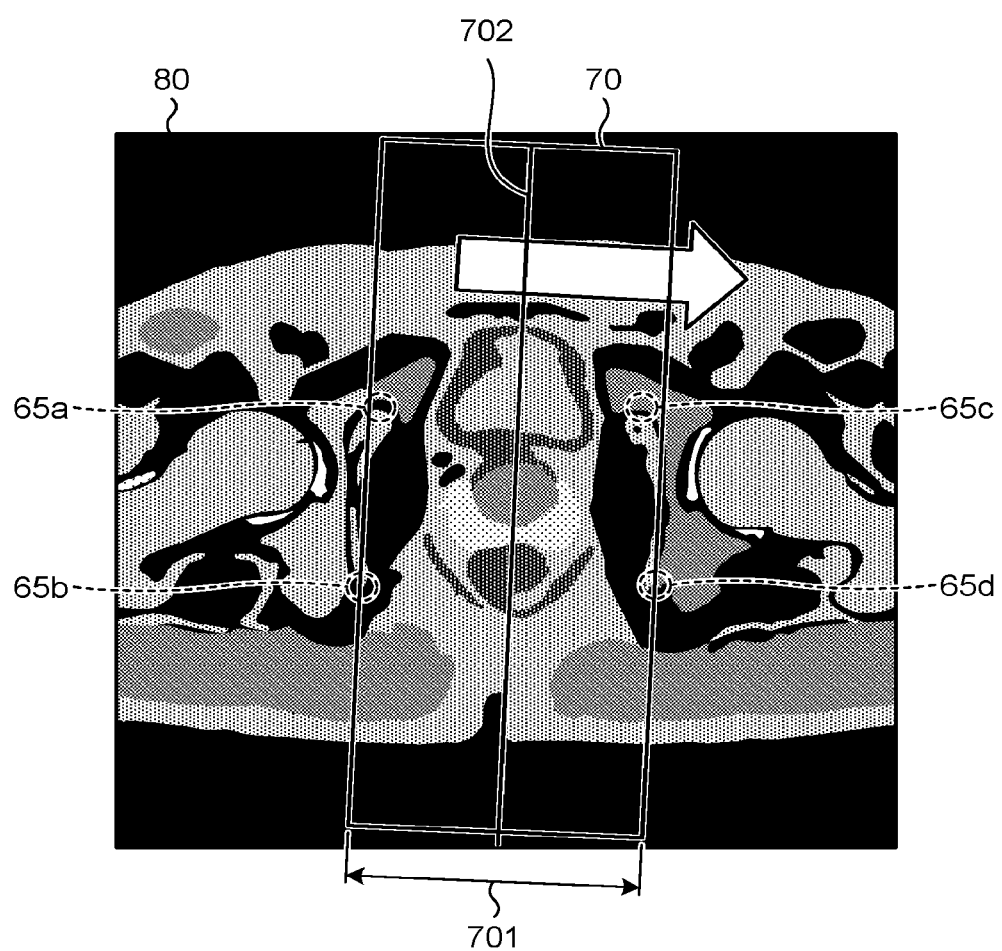
FIG. 11 is a drawing illustrating an example of a method for determining a slice width for taking a sagittal image according to the first embodiment.

FIG. 11 is a drawing illustrating an example of a method for determining the slice width 701 for taking the sagittal image according to the present embodiment. FIG. 11 illustrates the example with a body-axis cross-sectioning plane of the position-determining-purpose magnetic resonance image 80.

In FIG. 11, characteristic points 65a and 65c are positioned inside the pelvis and are sites corresponding to gaps between bones. Further, characteristic points 65b and 65d are projections positioned inside the pelvis. The characteristic points 65a and 65c are positioned on the front side of the patient P, whereas the characteristic points 65b and 65d are positioned on the back side of the patient P.

The prostate is positioned between the characteristic points 65a and 65d of the pelvis and the characteristic points 65c and 65b positioned so as to face the characteristic points 65a and 65d, respectively, while the spine is interposed therebetween. Accordingly, by setting the slice width 701 so that the region to be imaged 70 contains the region positioned between the characteristic points 65a and 65d and the characteristic points 65c and 65b of the pelvis, the determining function 133c is able to set the region to be imaged 70 for taking the sagittal image while ensuring that the prostate of the patient P is included.

For example, among various slice widths 701 that allow all the characteristic points 65a to 65d to be contained in the region to be imaged 70, the determining function 133c determines the narrowest slice width 701 as the slice width 701 for taking the diagnosis-purpose sagittal image.

However, possible conditions used for determining the slice width 701 are not limited to this example. For instance, the determining function 133c may set the slice width 701 so that the contour lines of the region to be imaged 70 on the two lateral sides pass through all the characteristic points 65a to 65d. Alternatively, for example, the determining function 133c may set the slice width 701 so as to minimize a total of the distances between the contour lines of the region to be imaged 70 on the two lateral sides and each of the characteristic points 65a to 65d.

Further, possible characteristic points of the pelvis used as a reference for determining the slice width 701 are not limited to the characteristic points 65a to 65d illustrated in FIG. 11. It is acceptable to use other characteristic points as a reference as long as the characteristic points can easily be detected from the position-determining-purpose magnetic resonance image 80.

The determining function 133c is configured to send, to the imaging processing function 133a, the results of determining the slice direction, the slice center, the slice width, and the rotation amount of the imaged cross-sectional plane in the in-plane direction to be used for taking each of the diagnosis-purpose axial, sagittal, and coronal images.

Returning to the description of FIG. 1, the display controlling function 133d is configured to cause the display 135 to display an image indicating the region to be imaged 70 determined by the determining function 133c. For example, the display controlling function 133d causes the display 135 to display an image in which the region to be imaged 70 for taking each of the diagnosis-purpose axial, sagittal, and coronal images is superimposed on the position-determining-purpose magnetic resonance image 80. However, possible modes of display are not limited to this example.

Further, after the main imaging process is performed by the imaging processing function 133a, the display controlling function 133d is configured to cause the display 135 to display the diagnosis-purpose magnetic resonance images taken in the main imaging process.

The receiving function 133e is configured to receive various types of operations performed by the user via the input interface 134. More specifically, the receiving function 133e is configured to receive operations performed by the user to change any of the slice direction, the slice center, the slice width, and the rotation amount of the imaged cross-sectional plane in the in-plane direction of the region to be imaged 70 determined by the determining function 133c. For example, the receiving function 133e may receive an operation performed by the user to change the position, the size, the tilt, or the like of the region to be imaged 70 displayed on the display 135, as an operation to change any of the slice direction, the slice center, the slice width, and the rotation amount of the imaged cross-sectional plane in the in-plane direction.

Further, the receiving function 133e is configured to receive an operation performed by the user to instruct that the position determining process be completed. For example, the receiving function 133e is configured to receive an operation of the user to click with a mouse or the like on an imaging start button displayed on the display 135, as the operation to instruct that the position determining process be completed. Alternatively, the imaging start button may be provided as a physical button on the magnetic resonance imaging apparatus 100, instead of as the image.

In the explanations above, the example was explained in which the "processing circuitry" is configured to read and execute the programs corresponding to the functions from the storage. However, possible embodiments are not limited to this example. The term "processing circuitry" denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). When the processing circuitry is a CPU, for example, the processing circuitry is configured to realize the functions by reading and executing the programs saved in the storage. Alternatively, when the processing circuitry is an ASIC, the functions are directly incorporated, as logic circuitry, into the circuit of the processing circuitry, instead of the programs being saved in the storage. The pieces of processing circuitry according to the present embodiment do not each necessarily have to be structured as a single circuit. It is also acceptable to structure one piece of processing circuitry by combining together a plurality of independent circuits, so as to realize the functions thereof. Further, two or more of the constituent elements illustrated in FIG. 1 may be integrated in a single piece of processing circuitry so as to realize the functions thereof.

Next, the following will describe a flow in a position determining process performed by the magnetic resonance imaging apparatus 100 according to the present embodiment configured as described above.

Figure 12:
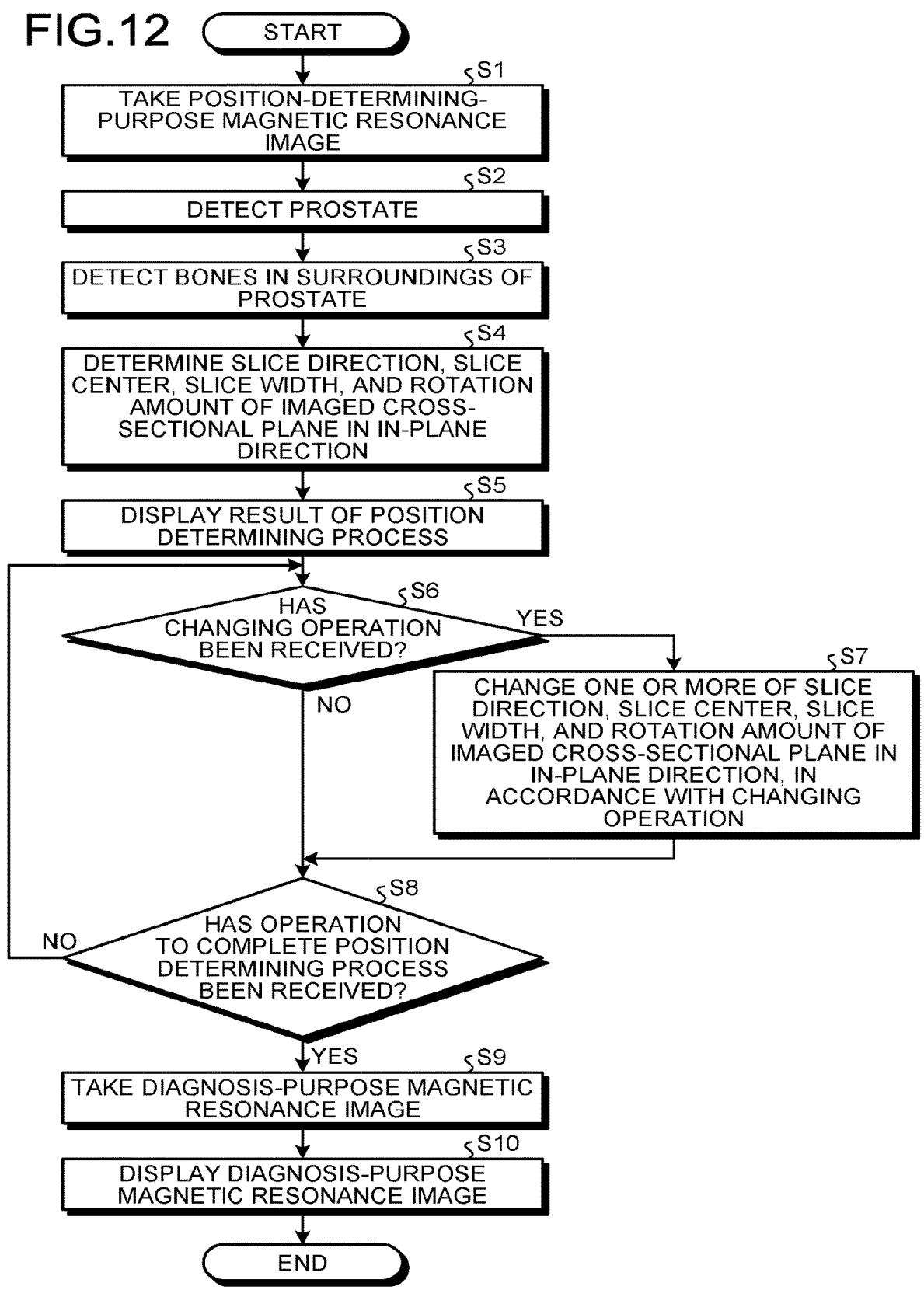
FIG. 12 is a flowchart illustrating an example of a flow in a position determining process according to the first embodiment.

FIG. 12 is a flowchart illustrating an example of the flow in the position determining process according to the present embodiment. As a premise of this flowchart, it is assumed that the patient P is placed on the couchtop 105a, while the couchtop 105a is inserted in the image taking opening.

To begin with, the imaging processing function 133a takes a position-determining-purpose magnetic resonance image 80 (step S1).

After that, from the position-determining-purpose magnetic resonance image 80 that was taken, the detecting function 133b detects the prostate by implementing an image processing process such as template matching or by using a trained model (step S2).

Further, from the position-determining-purpose magnetic resonance image 80 that was taken, the detecting function 133b detects bones (the femoral heads, the pelvis, the articular labra, and the pubic symphysis) in the surroundings of the prostate by implementing an image processing process such as template matching or by using the trained model 90 (step S3).

After that, on the basis of the positions of the tissues detected by the detecting function 133b within the position-determining-purpose magnetic resonance image 80, the determining function 133c determines a slice direction, a slice center, a slice width, and a rotation amount of an imaged cross-sectional plane in the in-plane direction to be used in the main imaging process (step S4).

Subsequently, the display controlling function 133d causes the display 135 to display a result of the position determining process performed by the determining function 133c (step S5). More specifically, the display controlling function 133d causes the display 135 to display an image indicating a region to be imaged 70 determined by the determining function 133c.

After that, the receiving function 133e judges whether or not a user operation has been received to change any of the slice direction, the slice center, the slice width, and the rotation amount of the imaged cross-sectional plane in the in-plane direction regarding the region to be imaged 70 determined by the determining function 133c (step S6).

Upon determining that a user operation has been received to change any of the slice direction, the slice center, the slice width, and the rotation amount of the imaged cross-sectional plane in the in-plane direction (step S6: "YES"), the receiving function 133e changes the designated one or more of the slice direction, the slice center, the slice width, and the rotation amount of the imaged cross-sectional plane in the in-plane direction, in accordance with the received changing operation (step S7).

After that, the receiving function 133e judges whether or not a user operation has been received to complete the position determining process (step S8). Also, when determining that no user operation has been received to change one or more of the slice direction, the slice center, the slice width, and the rotation amount of the imaged cross-sectional plane in the in-plane direction (step S6: "NO"), the receiving function 133e proceeds to the process at step S8.

Upon determining that no user operation has been received to complete the position determining process (step S8: "NO"), the receiving function 133e returns to the process at step S6.

On the contrary, upon determining that a user operation has been received to complete the position determining process (step S8: "YES"), the receiving function 133e informs the imaging processing function 133a that the position determining process is completed.

In this situation, on the basis of the region to be imaged 70 determined by the determining function 133c, the imaging processing function 133a takes a diagnosis-purpose magnetic resonance image (step S9). Further, when the user changed, at step S8, any of the slice direction, the slice center, the slice width, and the rotation amount of the imaged cross-sectional plane in the in-plane direction with respect to the region to be imaged 70, the imaging processing function 133a takes a diagnosis-purpose magnetic resonance image on the basis of the post-change region to be imaged 70. Alternatively, it is also acceptable to omit the function of receiving changes made by the user on the region to be imaged 70. The imaging processing function 133a may thus use the region to be imaged 70 determined by the determining function 133c without any change. When the function of receiving changes made by the user on the region to be imaged 70 is omitted, the display 135 does not necessarily have to display the image indicating the imaging region to be imaged 70 determined by the determining function 133c. The imaging processing function 133a saves the diagnosis-purpose magnetic resonance image that was taken, into the storage 132.

Further, the display controlling function 133d causes the display 135 to display the diagnosis-purpose magnetic resonance image taken by the imaging processing function 133a (step S10). The process in the flowchart has thus ended.

As explained above, from the position-determining-purpose magnetic resonance image 80, the magnetic resonance imaging apparatus 100 according to the present embodiment is configured to detect at least one tissue from among the femoral heads, the pelvis, the articular labra, the pubic symphysis, the urethra, and the apex of the prostate of the patient P and to further determine the region to be imaged 70 to be used for taking the diagnosis-purpose magnetic resonance image on the basis of the detected tissue. As a result, by using the magnetic resonance imaging apparatus 100 according to the present embodiment, it is possible to reduce the work of the user (e.g., a technologist) during the position determining process performed by trial and error on the position-determining-purpose magnetic resonance image 80. It is therefore possible to reduce the workload of the user in the position determining process at the time of taking the MR images of the prostate.

Further, when the magnetic resonance imaging apparatus 100 according to the present embodiment is used, because the reference with which the position is determined is unified, even when the MR imaging process is performed on the patient P multiple times, it is easier to perform the imaging process in the same position as the positions used in the previous imaging processes, compared to the situation where the user manually performs the position determining process. Consequently, by using the magnetic resonance imaging apparatus 100 according to the present embodiment, it is possible to enhance reproducibility of the position determining process.

More specifically, the magnetic resonance imaging apparatus 100 according to the present embodiment is configured to determine at least one of: the slice direction, the slice center, the slice width, and the rotation amount of the imaged cross-sectional plane in the in-plane direction to be used for taking the diagnosis-purpose two-dimensional magnetic resonance images. Consequently, by using the magnetic resonance imaging apparatus 100 according to the present embodiment, it is possible to reduce the workload of the user in the position determining process regarding at least the one of the slice direction, the slice center, the slice width, and the rotation amount of the imaged cross-sectional plane in the in-plane direction.

Further, the magnetic resonance imaging apparatus 100 according to the present embodiment is configured to determine the direction perpendicular to the line segment 600 passing through the respective upper end parts 60a and 60b of the two femoral heads of the patient P, as the slice direction for taking the diagnosis-purpose axial image. Consequently, by using the magnetic resonance imaging apparatus 100 according to the present embodiment, it is possible to set the slice direction suitable for taking the diagnosis-purpose axial image of the prostate.

Furthermore, the magnetic resonance imaging apparatus 100 according to the present embodiment is configured to determine the slice width for taking the diagnosis-purpose axial image, on the basis of the positions of the two femoral heads and the position of the pubic symphysis of the patient P. Consequently, by using the magnetic resonance imaging apparatus 100 according to the present embodiment, it is possible to set the slice width 701 suitable for taking the diagnosis-purpose axial image of the prostate.

In addition, the magnetic resonance imaging apparatus 100 according to the present embodiment is configured to determine the rotation amount of the imaged cross-sectional plane in the in-plane direction of the region to be imaged 70, for taking the diagnosis-purpose axial image, on the basis of the plurality of articular labra 62a to 62d of the patient P. Consequently, by using the magnetic resonance imaging apparatus 100 according to the present embodiment, it is possible to set the rotation amount of the imaged cross-sectional plane in the in-plane direction suitable for taking the diagnosis-purpose axial image of the prostate.

Also, among the plurality of articular labra 62a to 62d of the patient P, the magnetic resonance imaging apparatus 100 according to the present embodiment is configured to obtain the middle point 63a of the line segment 621a connecting together the articular labrum 62a and the articular labrum 62b and the middle point 63b of the line segment 621b connecting together the articular labrum 62c and the articular labrum 62d, each of the pairs of articular labra facing each other along the width direction of the body of the patient P. In addition, the magnetic resonance imaging apparatus 100 is configured to determine the direction perpendicular to the line segment 601 connecting together the two obtained middle points 63a and 63b as the slice direction for taking the diagnosis-purpose sagittal image. Consequently, by using the magnetic resonance imaging apparatus 100 according to the present embodiment, it is possible to set the slice direction suitable for taking the diagnosis-purpose sagittal image of the prostate.

Further, on the basis of the characteristic points 65a to 65d of the pelvis of the patient P, the magnetic resonance imaging apparatus 100 according to the present embodiment is configured to determine the slice width 701 for taking the diagnosis-purpose sagittal image of the prostate. Consequently, by using the magnetic resonance imaging apparatus 100 according to the present embodiment, it is possible to set the slice width 701 suitable for taking the diagnosis-purpose sagittal image of the prostate.

Furthermore, the magnetic resonance imaging apparatus 100 according to the present embodiment is configured to determine the slice center 702 for taking the diagnosis-purpose sagittal image of the prostate to be in the position passing through the center of the prostate of the patient P. Consequently, by using the magnetic resonance imaging apparatus 100 according to the present embodiment, it is possible to set the slice center 702 suitable for taking the diagnosis-purpose sagittal image of the prostate.

In addition, when the slice center 702 determined on the basis of the detected position of the prostate is apart from the detected position of the pubic symphysis by a distance equal to or longer than the prescribed length, the magnetic resonance imaging apparatus 100 according to the present embodiment is configured to correct the position of the slice center 702 on the basis of the detected position of the pubic symphysis. Consequently, by using the magnetic resonance imaging apparatus 100 according to the present embodiment, it is possible to set the slice center 702 suitable for taking the diagnosis-purpose sagittal image of the prostate with a higher level of precision.

Also, among the plurality of articular labra 62a to 62d of the patient P, the magnetic resonance imaging apparatus 100 according to the present embodiment is configured to obtain the middle point 63c of the line segment 621c connecting together the articular labrum 62a and the articular labrum 62c and the middle point 63d of the line segment 621d connecting together the articular labrum 62b and the articular labrum 62d, each of the pairs of articular labra facing each other along the front-and-back direction of the body of the patient P. Further, the magnetic resonance imaging apparatus 100 is configured to determine the direction perpendicular to the line segment 602 connecting together the two obtained middle points 63c and 63d, as the slice direction for taking the diagnosis-purpose coronal image. Consequently, by using the magnetic resonance imaging apparatus 100 according to the present embodiment, it is possible to set the slice direction suitable for taking the diagnosis-purpose coronal image of the prostate.

Further, the magnetic resonance imaging apparatus 100 according to the present embodiment is configured to determine the slice width 701 of the coronal image on the basis of the position of the pubic symphysis in the front-and-back direction of the body of the patient P. Consequently, by using the magnetic resonance imaging apparatus 100 according to the present embodiment, it is possible to set the slice width 701 suitable for taking the diagnosis-purpose coronal image of the prostate.

Furthermore, the magnetic resonance imaging apparatus 100 according to the present embodiment is configured to take each of the diagnosis-purpose magnetic resonance images on the basis of the region to be imaged 70 determined on the basis of the tissues detected from the position-determining-purpose magnetic resonance image 80. Consequently, by using the magnetic resonance imaging apparatus 100 according to the present embodiment, it is possible, in the main imaging process, to take images of the region to be imaged 70 suitable for imaging the prostate of the patient P.

In addition, the magnetic resonance imaging apparatus 100 according to the present embodiment is configured to cause the display 135 to display the image indicating the region to be imaged 70 determined on the basis of the tissues detected from the position-determining-purpose magnetic resonance image 80. Consequently, by using the magnetic resonance imaging apparatus 100 according to the present embodiment, the user is able to check the results of the position determining process that was automatically executed.

Also, the magnetic resonance imaging apparatus 100 according to the present embodiment is configured to detect at least one tissue from among the femoral heads, the pelvis, the articular labra, the pubic symphysis, the urethra, and the apex of the prostate of the patient P rendered in the position-determining-purpose magnetic resonance image 80, by inputting the position-determining-purpose magnetic resonance image 80 to the trained model 90. Consequently, by using the magnetic resonance imaging apparatus 100 according to the present embodiment, it is possible to detect the tissues rendered in the position-determining-purpose magnetic resonance image 80 with a high level of precision.

In this situation, the trained model 90 according to the present embodiment includes a "self-learning model" configured to further update an internal algorithm of the trained model 90 by obtaining user feedback on the estimation results. For example, when the user changes any of the slice direction, the slice center, the slice width, and the rotation amount of the imaged cross-sectional plane in the in-plane direction, the trained model 90 may update the internal algorithm of the trained model 90 according to the content of the change.

Further, the trained model 90 may be generated by a device provided outside the magnetic resonance imaging apparatus 100 so as to be input to the magnetic resonance imaging apparatus 100. In another example, the processing circuit 133 of the magnetic resonance imaging apparatus 100 may further have a learning function configured to generate the trained model 90.

Alternatively, the trained model 90 may be constructed by an integrated circuit such as an ASIC or an FPGA. In other examples, it is also acceptable to use a mathematical model, a lookup table, a database, or the like in place of the trained model 90.

Furthermore, the trained model 90 or the template images used in the detecting process may be stored in a storage device provided outside the magnetic resonance imaging apparatus 100.

Second Embodiment

In the first embodiment above, the example was explained in which the determining function 133c of the magnetic resonance imaging apparatus 100 is configured to perform the position determining process on the basis of the femoral heads, the pelvis, the articular labra, the pubic symphysis, the urethra, and the apex of the prostate of the patient P detected from the position-determining-purpose magnetic resonance image 80. In a second embodiment, the determining function 133c of the magnetic resonance imaging apparatus 100 is further configured to perform a position determining process on the basis of the urethra and the apex of the prostate.

A configuration of the magnetic resonance imaging apparatus 100 according to the present embodiment is the same as the configuration in the first embodiment explained with reference to FIG. 1. Further, the processing circuitry 133 of the magnetic resonance imaging apparatus 100 according to the present embodiment includes, similarly to the first embodiment, the imaging processing function 133a, the detecting function 133b, the determining function 133c, the display controlling function 133d, and the receiving function 133e. The imaging processing function 133a, the display controlling function 133d, and the receiving function 133e according to the present embodiment have the same functions as those in the first embodiment.

In addition to the functions described in the first embodiment, the detecting function 133b according to the present embodiment is configured to detect the urethra and the apex of the prostate of the patient P, from a position-determining-purpose magnetic resonance image 80.

Further, in addition to the functions described in the first embodiment, the determining function 133c according to the present embodiment is configured to determine slice directions for taking a diagnosis-purpose axial image and a diagnosis-purpose coronal image, on the basis of the urethra and the apex of the prostate of the patient P detected by the detecting function 133b.

Figure 13:
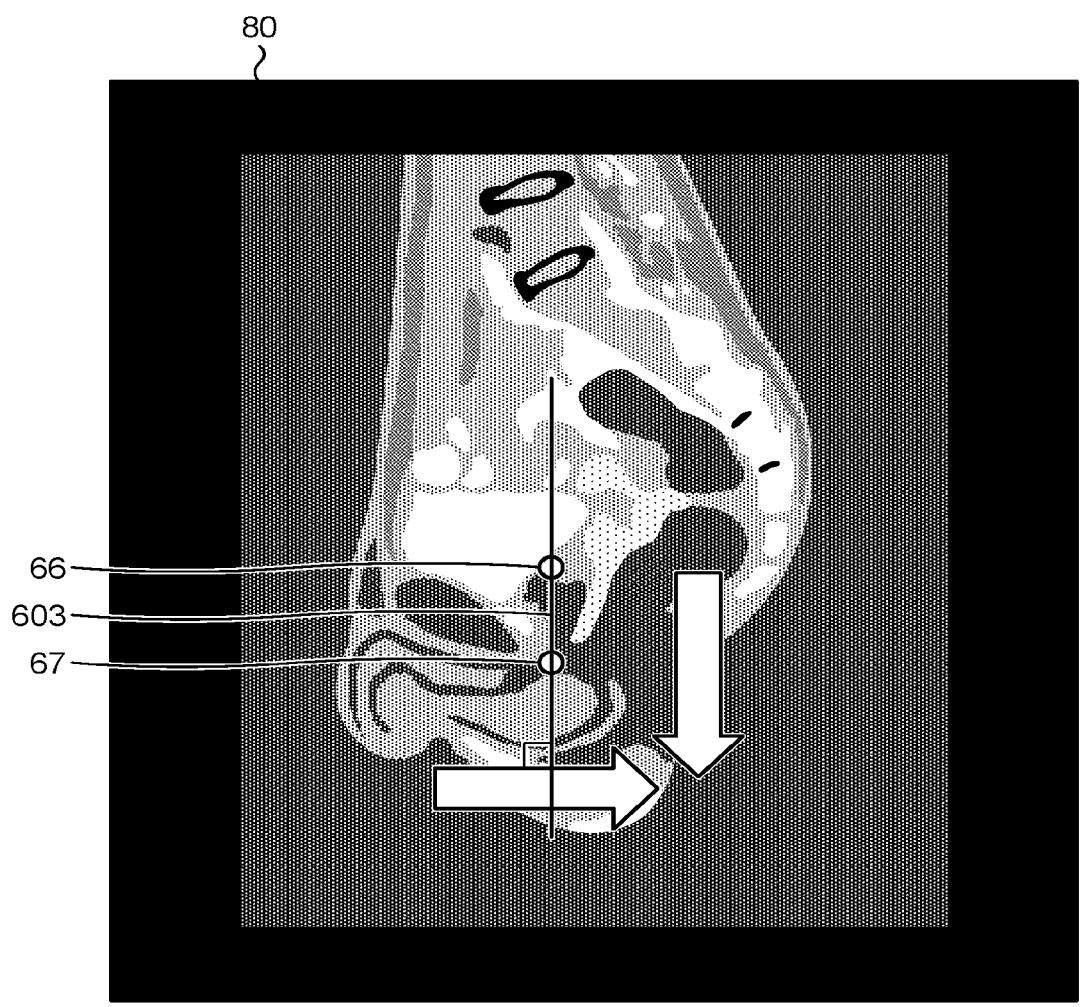
FIG. 13 is a drawing illustrating an example of a method for determining slice directions of a coronal image and an axial image according to a second embodiment.

FIG. 13 is a drawing illustrating an example of a method for determining the slice directions of the coronal image and the axial image according to the present embodiment. FIG. 13 illustrates the example with a sagittal cross-section of a position-determining-purpose magnetic resonance image 80.

As illustrated in FIG. 13, the determining function 133c is configured to obtain a line segment 603 connecting a start position 66 of the urethra to the apex of the prostate 67 of the patient P, within the sagittal cross-section of the position-determining-purpose magnetic resonance image 80.

The determining function 133c is configured to determine the direction parallel to the line segment 603 as the slice direction for taking the diagnosis-purpose axial image. Further, the determining function 133c is configured to determine the direction perpendicular to the line segment 603 as the slice direction for taking the diagnosis-purpose coronal image.

As explained above, when the magnetic resonance imaging apparatus 100 according to the present embodiment is used, the slice directions for taking the diagnosis-purpose axial image and the diagnosis-purpose coronal image are determined on the basis of the urethra and the apex of the prostate of the patient P. As a result, while keeping the advantageous effects of the first embodiment, it is possible to obtain the slice positions for the diagnosis-purpose axial image and the diagnosis-purpose coronal image that are further suitable for a diagnosing process on the prostate.

Modification Examples

In the first and the second embodiments above, the example was explained in which the magnetic resonance imaging apparatus 100 is configured to perform the position determining process. However, a part or all of the position determining process may be performed by an apparatus other than the magnetic resonance imaging apparatus 100. For example, another information processing apparatus connected to the magnetic resonance imaging apparatus 100 via a network or the like may include the detecting function 133b or the determining function 133c.

Further, in the first and the second embodiments above, the example was explained in which the display controlling function 133d is configured to cause the display 135 to display the image indicating the region to be imaged 70. However, the image may be displayed by another display connected to the magnetic resonance imaging apparatus 100 via a network or the like. In that situation, the other display is an example of the display.

Furthermore, in the first and the second embodiments above, the example was explained in which the trained model 90 is saved in the storage 132. However, the trained model 90 may be incorporated in the detecting function 133b.

According to at least one aspect of the embodiments described above, it is possible to reduce the workload of the user in the position determining process at the time of taking the MR images of the prostate.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus, comprising:
a coil configured to receive a magnetic resonance signal emitted from a subject due to influence of a radio frequency magnetic field; and
processing circuitry configured to
detect at least one tissue from among a femoral head, a pelvis, an articular labrum, a pubic symphysis, a urethra, and an apex of a prostate of the subject, from a locator image generated based on the magnetic resonance signal and including the prostate of the subject,
determine a region to be imaged of the prostate of the subject, based on the detected at least one tissue; and
perform a scan using the coil to generate a magnetic resonance image of the determined region of the prostate, wherein
the region to be imaged corresponds to a two-dimensional magnetic resonance image,
the processing circuitry is further configured to determine at least one of: a slice direction, a slice center, a slice width, and a rotation amount of an imaged cross-sectional plane in an in-plane direction, for generating the two-dimensional magnetic resonance image,
the two-dimensional magnetic resonance image includes an axial image,
the processing circuitry is further configured to detect two femoral heads of the subject from the locator image, and
the processing circuitry is further configured to determine a direction perpendicular to a line segment passing through respective upper end parts of the two femoral heads, as a slice direction for generating the axial image.

2. The magnetic resonance imaging apparatus according to claim 1, wherein
the processing circuitry is further configured to detect the pubic symphysis of the subject from the locator image, and
the processing circuitry is further configured to determine a slice width for generating the axial image based on positions of the two femoral heads and a position of the pubic symphysis.

3. The magnetic resonance imaging apparatus according to claim 1, wherein
the processing circuitry is further configured to detect a plurality of articular labra of the subject from the locator image, and
the processing circuitry is further configured to determine a rotation amount in the in-plane direction for generating the axial image, on a basis of the plurality of articular labra.

4. The magnetic resonance imaging apparatus according to claim 1, wherein the processing circuitry is further configured to perform a process of generating the magnetic resonance image, based on the determined region to be imaged.

5. The magnetic resonance imaging apparatus according to claim 1, wherein the processing circuitry is further configured to cause a display to display the magnetic resonance image of the determined region.

6. The magnetic resonance imaging apparatus according to claim 1, wherein the processing circuitry is further configured to detect said at least one tissue from among the femoral head, the pelvis, the articular labrum, the pubic symphysis, the urethra, and the apex of a prostate of the subject within the locator image, by inputting the locator image into a trained model that was previously trained using a training-purpose magnetic resonance image having an image region including at least one of the femoral head, the pelvis, the articular labrum, the pubic symphysis, the urethra, and the apex of the prostate.

7. A magnetic resonance imaging apparatus, comprising:
a coil configured to receive a magnetic resonance signal emitted from a subject due to influence of a radio frequency magnetic field; and
processing circuitry configured to
detect at least one tissue from among a femoral head, a pelvis, an articular labrum, a pubic symphysis, a urethra, and an apex of a prostate of the subject, from a locator image generated based on the magnetic resonance signal and including the prostate of the subject,
determine a region to be imaged of the prostate of the subject, based on the detected at least one tissue; and
perform a scan using the coil to generate a magnetic resonance image of the determined region of the prostate, wherein
the region to be imaged corresponds to a two-dimensional magnetic resonance image,
the processing circuitry is further configured to determine at least one of: a slice direction, a slice center, a slice width, and a rotation amount of an imaged cross-sectional plane in an in-plane direction, for generating the two-dimensional magnetic resonance image,
the two-dimensional magnetic resonance image includes a sagittal image,
the processing circuitry is further configured to detect a plurality of articular labra of the subject from the locator image, and
the processing circuitry is further configured to obtain a middle point of each of two line segments connecting together two articular labra among the plurality of articular labra that face each other along a width direction of a body of the subject and further determines a direction perpendicular to a line segment connecting together the two obtained middle points as a slice direction for generating the sagittal image.

8. The magnetic resonance imaging apparatus according to claim 7, wherein
the processing circuitry is further configured to detect the pelvis of the subject from the locator image, and
the processing circuitry is further configured to determine the slice width for generating the sagittal image based on a characteristic point of the pelvis.

9. The magnetic resonance imaging apparatus according to claim 7, wherein
the processing circuitry is further configured to detect the prostate of the subject from the locator image, and
the processing circuitry is further configured to determine the slice center for generating the sagittal image to be in a position passing through a center of the detected prostate.

10. The magnetic resonance imaging apparatus according to claim 9, wherein
the processing circuitry is further configured to detect the pubic symphysis of the subject from the locator image, and
the processing circuitry is further configured to correct the position of the slice center based on the position of the detected pubic symphysis, when the slice center determined based on a position of the detected prostate is apart from a position of the detected pubic symphysis by a distance equal to or longer than a prescribed length.

11. A magnetic resonance imaging apparatus, comprising:
a coil configured to receive a magnetic resonance signal emitted from a subject due to influence of a radio frequency magnetic field; and
processing circuitry configured to
detect at least one tissue from among a femoral head, a pelvis, an articular labrum, a pubic symphysis, a urethra, and an apex of a prostate of the subject, from a locator image generated based on the magnetic resonance signal and including the prostate of the subject,
determine a region to be imaged of the prostate of the subject, based on the detected at least one tissue; and
perform a scan using the coil to generate a magnetic resonance image of the determined region of the prostate, wherein
the region to be imaged corresponds to a two-dimensional magnetic resonance image,
the processing circuitry is further configured to determine at least one of: a slice direction, a slice center, a slice width, and a rotation amount of an imaged cross-sectional plane in an in-plane direction, for generating the two-dimensional magnetic resonance image,
the two-dimensional magnetic resonance image includes a coronal image,
the processing circuitry is further configured to detect a plurality of articular labra of the subject from the locator image, and
the processing circuitry is further configured to obtain a middle point of each of two line segments connecting together two articular labra among the plurality of articular labra that face each other along a front-and-back direction of a body of the subject, and further determine a direction perpendicular to a line segment connecting together the two obtained middle points as a slice direction for generating the coronal image.

12. The magnetic resonance imaging apparatus according to claim 11, wherein
the processing circuitry is further configured to detect the pubic symphysis of the subject from the locator image, and
the processing circuitry is further configured to determine a slice width of the coronal image based on a position of the pubic symphysis in the front-and-back direction of the body of the subject.

* * * * *